(12) United States Patent
Jensen (10) Patent No.: US 7,650,702 B2
(45) Date of Patent: Jan. 26, 2010

(54) OSTOMY SUPPORT GARMENT AND THE PREPARATION THEREOF

(75) Inventor: Henrik Jessen Jensen, Birkeroed (DK)

(73) Assignee: Coloplast A/S, Humlebaek (DK)

( * ) Notice: Subject to any disclaimer, the term of this patent is extended or adjusted under 35 U.S.C. 154(b) by 476 days.

(21) Appl. No.: 10/544,342

(22) PCT Filed: Feb. 3, 2004

(86) PCT No.: PCT/DK2004/000072

§ 371 (c)(1),
(2), (4) Date: Aug. 3, 2005

(87) PCT Pub. No.: WO2004/069115

PCT Pub. Date: Aug. 19, 2004

(65) Prior Publication Data

US 2006/0107445 A1    May 25, 2006

(30) Foreign Application Priority Data

Feb. 3, 2003    (DK) ............................... 2003 00145

(51) Int. Cl.
*A61F 5/449* (2006.01)
*A41B 9/00* (2006.01)

(52) U.S. Cl. ............................. 33/566; 33/512; 33/2 R; 33/12; 2/400; 604/345

(58) Field of Classification Search .................. 33/566, 33/562, 563, 511, 512, 515, 2 R, 11, 12; 2/400, 2/114, 401–403, 405, 406, 408, 465, 23; 604/343, 345, 116, 327, 332, 337
See application file for complete search history.

(56) References Cited

U.S. PATENT DOCUMENTS

| 2,778,362 | A | * | 1/1957 | Pollock et al. ............... 604/345 |
| 3,324,856 | A |   | 6/1967 | Young |
| 3,500,550 | A | * | 3/1970 | Mihai ........................... 33/662 |
| 3,798,781 | A | * | 3/1974 | Wolfe ........................... 33/563 |
| 4,064,631 | A | * | 12/1977 | Gebert .......................... 33/2 R |
| 4,533,355 | A | * | 8/1985 | Fair ............................. 604/345 |
| 4,779,346 | A |   | 10/1988 | Schafer |
| 4,790,694 | A |   | 12/1988 | Wilent et al. |
| 5,135,520 | A |   | 8/1992 | Beaupied |
| 5,606,748 | A |   | 3/1997 | Fujiwara |
| 5,749,149 | A |   | 5/1998 | Claytor |
| 6,041,445 | A | * | 3/2000 | Davitt ........................... 2/400 |
| 6,202,222 | B1 |  | 3/2001 | Robbins |

(Continued)

FOREIGN PATENT DOCUMENTS

DE    3401 353 A1    7/1985

(Continued)

*Primary Examiner*—Amy Cohen Johnson
(74) *Attorney, Agent, or Firm*—Coloplast Corp., Coloplast A/S; Daniel G. Chapik; Nicholas R. Baumann (57) ABSTRACT

A device for locating and marking the optimum position of the center of a hole for receiving a stoma in a hernia support, said device being in the form of work piece provided with a pattern for identifying and recording the optimum position for placing of the center of the hole provides a simple device and method for an easy determination and marking of the site for a customized hole in standard hernia trousers.

8 Claims, 5 Drawing Sheets

U.S. PATENT DOCUMENTS

| | | |
|---|---|---|
| 6,276,175 B1 | 8/2001 | Browder, Jr. |
| 6,311,408 B1 * | 11/2001 | Madayag ............... 33/653 |
| 6,415,450 B1 * | 7/2002 | Lien ............... 2/400 |
| 6,540,756 B1 * | 4/2003 | Vaughan ............... 606/116 |
| 6,635,050 B1 | 10/2003 | Jensen et al. |
| 6,659,989 B1 | 12/2003 | Otto |
| 6,745,406 B2 * | 6/2004 | Ruane ............... 2/465 |
| 7,198,614 B2 * | 4/2007 | Kappauf ............... 604/116 |
| 7,310,885 B2 * | 12/2007 | Tedesco et al. ............... 33/2 R |
| 7,313,832 B2 * | 1/2008 | Worsoee ............... 2/400 |
| 2002/0157273 A1* | 10/2002 | Noyes ............... 33/759 |
| 2006/0048283 A1* | 3/2006 | Sorensen ............... 2/400 |

FOREIGN PATENT DOCUMENTS

| | | |
|---|---|---|
| DE | 3439 373 A1 | 5/1986 |
| DE | 200 15 482 U1 | 11/2000 |
| DE | 100 51 080 C1 | 3/2002 |
| DK | 174536B B1 | 5/2003 |
| EP | 0 324 561 | 7/1989 |
| GB | 2 366 248 A | 8/2000 |
| GB | 2427537 A * | 1/2007 |
| JP | 5138503 | 6/1993 |
| JP | 200146415 | 2/2001 |
| WO | WO 00/25709 | 5/2000 |
| WO | WO 00/65940 | 11/2000 |
| WO | WO 00/67683 | 11/2000 |

* cited by examiner

OSTOMY SUPPORT GARMENT AND THE PREPARATION THEREOF

This is a nationalization of PCT/DK04/000072 filed Feb. 3, 2004 and published in English.

BACKGROUND OF THE INVENTION

1. Field of the Invention

The present invention relates to a device and a method for locating and marking the optimum position of the centre of a hole for receiving a stoma in stomal hernia support garment, especially stomal hernia support trousers and a set for use for locating and marking the optimum position of the centre of a hole for receiving a stoma in stomal hernia support garment.

In connection with surgery for a number of diseases in the gastrointestinal tract a consequence is, in many cases, that the colon, the ileum or the urethra has been exposed surgically and the patient is left with an abdominal stoma. Such artificial openings or fistulae cannot be controlled at will and are therefore of necessity incontinent and the effluents or waste products of the body, which are conveyed through these organs, are discharged through the artificial orifice or opening and are collected in a collection bag. Said bag which is usually adhered to the skin by means of an adhesive wafer or plate having an inlet opening for accommodating the stoma. Such appliances may be two-piece or one-piece appliances. In both types of appliances, a body side member is attached to the wearer's abdomen, and a receiving member or bag is attached to the body side ostomy member for receiving exudates from the stoma. Said receiving in case of a two-piece appliance.

In many instances patients having had a surgery resulting in the formation of a stoma, an accompanying condition is formation of a peristomal bulge or hernia, which may complicate the bandaging of the stoma and even require further surgery. Even if further surgery is carried out there is a considerable risk of a permanent condition, which cannot be alleviated.

In such cases, the patient will have to rely on an additional hernia support for a mechanical reposition of the bulge or hernia for reducing the risk of constriction or strangulation calling for urgent surgery and for providing a plane surface around the stoma for application of a collecting appliance in order to secure a proper adherence and sealing. Stomal bulge or hernia supports are commonly known and may e.g. be in the form of a belt of e.g. of leather with buckles or in the form of a support garment made from an elastic fabric being able to apply a sufficient pressure around the stoma.

In the case of a colostomy and in case the ostomate is normally irrigating, a minor cap or collecting bag may be used which enables the use of a firm support belt or tight compression briefs for providing a sufficient pressure around the stoma. For ileostomates or urostomates this procedure is not practicable due to the constant rather high output from the ileum or bladder and for urostomates it may be critical to provide a free flow from the stoma in order to prevent a build-up of a backpressure, which may destroy the kidneys.

In such cases, it is highly desirable or mandatory to give access to a larger collecting volume, which means that the collecting bag itself will have to be situated outside the pressure establishing belt or briefs and that a passageway through the same has to be established.

Determination of the site for placing the stoma is normally carried out prior to the operation after observing the patient in different postures, e.g. sitting, standing and bending over, finding the less critical area. WO 00/67683 discloses a device for use in the determination of the optimum position of a stoma-to-be for the patient in question.

As the placing of a stoma is not standardised but depends on the condition and the topography of the abdominal area of the patient, it is not possible to provide a simple selection of standard bulge or hernia supports having passageways fitting the majority of patients. The passageways must be precisely tailored according to the actual conditions of the individual patient.

2. Description of the Related Art

DK Patent Application No. PA 1999 01559 discloses a stomal hernial support compression garment in the form of a pair of customised compression trousers. The trousers are tailored by determining the dimensions of the patient and the localisation of the stoma for producing a pair of trousers specifically for the patient in question for ensuring a specific compression force. The manufacture of such a hernial support is laborious and expensive as the whole support is made specifically for each patient.

U.S. Pat. No. 5,135,520 discloses a variable closure device for an ostomy garment having a pair of criss-cross pocket forming panels configures to lie behind an ostomy device. The crisscross arrangement of pocket panels are created by finished edges which overlap along their lower ends to define an adjustable, elongated, slanted slot.

No devices for an easy location and marking of a hole for receiving a stoma for tailoring a hernia support from a standard support garment is disclosed and there is a need for such device in order to enable a simple, convenient, and cheap tailoring of hernia supports for improving the security against leakage and the quality of life for the patient after this kind of surgery.

The present invention provides a simple device and method for an easy determination and marking of the site for a customised hole in a standard support garment for enabling a free flow of effluents from a stoma to pass the hernia trousers without compromising the hernia supporting properties thereof. The invention also offers a simple, convenient, and reliable method for a decentralised collection of the necessary information and simple transfer thereof to the manufacturer for a centralised manufacture of customised support garments.

SUMMARY OF THE INVENTION

The Invention relates to a device for locating and marking the optimum position of the centre of a hole for receiving a stoma in a stomal hernia support.

Furthermore, the invention relates to a set for use for locating and marking the optimum position of the centre of a hole for receiving a stoma in a hernia support garment.

Still further, the invention relates to a methods for locating and marking the optimum position of the centre of a hole for receiving a stoma in support trousers and transferring the information for a central manufacture of customised support garments based on standard support garments.

BRIEF DESCRIPTION OF THE DRAWINGS

The invention is disclosed more in detail with reference to the drawings in which.

DETAILED DESCRIPTION OF THE PRESENT INVENTION

The invention relates to a device for locating and marking the optimum position of the centre of a hole for receiving a stoma in a stomal hernia support, said device being in the form of work piece provided with a pattern for identifying and recording the optimum position for placing of the centre of the hole.

The invention fulfils the requirements stated above and provides a simple, convenient, rapid and cheap method of providing customised ostomy support garments. Thus, it is not necessary to await the production of fully customised support garments and the manufacturer is rendered capable of rapid delivery of customised support garments from standard products without having to rely on a large stock of products.

In one embodiment of the invention the customised support piece is a garment provided whit holes for the legs of the user and may even be provided with trouser legs. In other embodiments the customised support piece is a piece without holes for the legs of the user such that the piece has a corset-like or belt-like shape.

In one embodiment of the invention, the device is in the form of stiff work piece being provided with a systematic pattern. The work piece is preferably of an essentially rectangular shape and provided with a printed pattern allowing an easy identification of a specific site at the surface, suitably a coordinate system. The pattern is suitably printed on the work piece. Such a work piece may suitably be used together with a sample standard pair of support briefs. The width of the work piece preferably corresponds to at least half the waist measurement of the briefs in which case it may be placed reproducibly in the briefs and flattening the same. Thus, the nurse or other assisting person only needs to have a sample of a work piece in the form of an essentially rectangular piece of e.g. cardboard provided with a coordinate system and a sample standard pair of support briefs which may be used several times for several ostomates. Then, after selecting and applying a standard pair of support briefs to the ostomate, locating and marking the optimum position of the centre of the hole for the receiving the stoma, the work piece is placed in the briefs and the coordinates and sizes of the support garment and the work piece may be recorded and stored and transferred to the manufacturer who may easily provide a corresponding pair of standard trousers with a tailored hole. The only Information, which has to be recorded and transferred to the manufacturer, is the coordinates of the centre of the hole and sizes of the support garment and the work piece. At the factory a corresponding essentially rectangular piece of e.g. cardboard provided with a coordinate system is then placed in a corresponding set of standard trousers and the site of the hole is then marked reproducibly and the hole produced and the edge stabilised against fraying in a manner known per se.

In accordance with a preferred embodiment of the invention, the device is in the form an essentially rectangular piece of foil or cardboard or paper or plastics material such as a sheet of a polyolefin such as polyethylene or polypropylene or polyvinyl chloride or a polyacrylate such as polymethyl methacrylate provided with a coordinate system which provides for an easy recording and storing of the information the position of the centre of the hole for the receiving the stoma as stated above.

In another embodiment of the invention, the device is in the form of piece of elastic fabric the size and stretchability of which corresponds to the size and stretchability of a standard pair of support briefs provided with a pattern suitable for recording the position of the centre of the hole for the receiving the stoma. Such a piece of elastic fabric may be used by wrapping the piece around the torso of an ostomate and covering the stoma, securing the same, and then marking the position of the stoma. It is preferred that the pattern is a coordinate system which provides for an easy recording and storing of the information the position of the centre of the hole.

In a preferred embodiment of the invention, the device is in the form of a pair of briefs of the same elastic fabric used for manufacturing stomal hernia trousers, which trousers are provided with a coordinate system. Then, after selecting and applying a pair of standard support briefs to the ostomate, locating and marking the optimum position of the centre of the hole for the receiving the stoma, the coordinates may be recorded and stored and transferred to the manufacturer who may easily provide the trousers with a tailored hole. Using this embodiment, it is possible to provide the standard briefs with a discreet pattern and then, standard briefs may be used for detecting and recording the site.

The pattern or coordinate system may be weaved in using a discreet tread of a different colour or printed on the surface of the trousers, preferably the inside. In a preferred embodiment, such a pattern is printed using ink, which is fluorescent and only visible when using UV light.

In a second aspect, the invention relates to a set for use for locating and marking the optimum position of the centre of a hole for receiving a stoma in a hernia support, said set comprising an essentially rectangular work piece provided with a coordinate system and an array of sample standard pairs of support briefs. Such a set is suitable for use as discussed above. For simplicity, it is preferred that the width of the work piece is sufficient to flatten all sizes of standard pairs of support briefs when placed inside the briefs.

In a third aspect, the invention relates to a method for locating and marking the optimum position of the centre of a hole for receiving a stoma in hernia trousers comprising placing a work piece around the torso of ostomate and covering the stoma, locating and recording the optimum position centre of the hole for the receiving the stoma and sizes of the support garment and the work piece, storing the information and using the same for producing a pair of stomal hernia trousers for the ostmate, said trousers having a tailored hole for receiving the stoma.

In a fourth aspect, the invention relates to a method for locating and marking the optimum position of the centre of a hole for receiving a stoma in hernia trousers comprising applying a pair of standard support briefs to the ostomate, locating and marking the optimum position of the centre of the hole for the receiving the stoma, placing a work piece of e.g. cardboard provided with a coordinate system in the briefs and recording the optimum coordinates of the centre of the hole and sizes of the support garment and the work piece, storing the information and using the same for producing a pair of stomal hernia trousers having a tailored hole for the ostomate.

In a fifth aspect, the invention relates to a method for locating and marking the optimum position of the centre of a hole for receiving a stoma in stomal hernia trousers comprising applying a pair of briefs of elastic fabric provided with a coordinate system, locating and marking the optimum position and recording the coordinates of the centre of the hole for the receiving the stoma, storing the information together with information on the size of the briefs and using the same for producing a pair of stomal hernia trousers for the ostomate.

DESCRIPTION OF THE PREFERRED EMBODIMENTS

The invention is now explained more in detail with reference to the drawings showing preferred embodiments of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
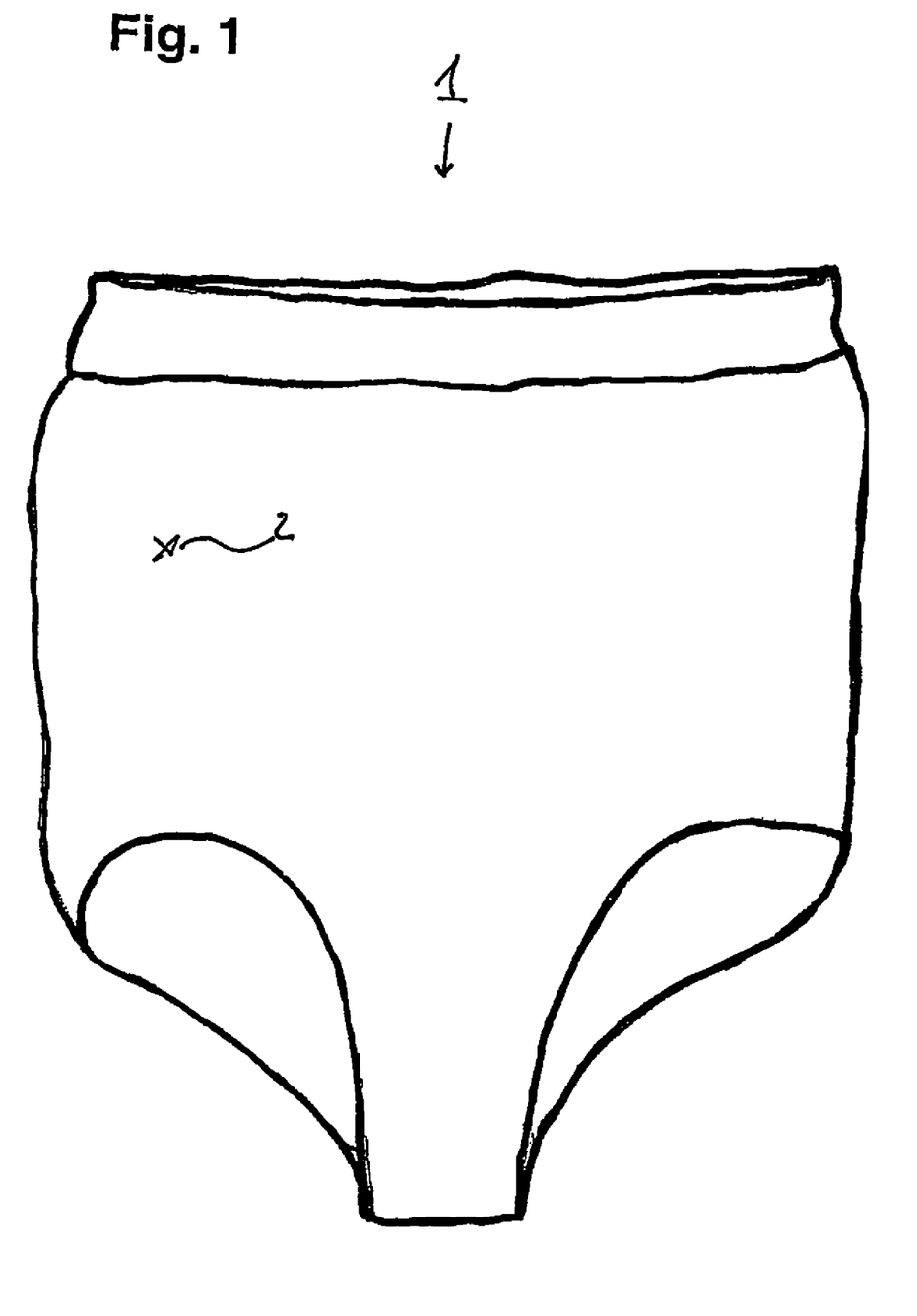
FIG. 1 shows a pair of stomal hernia trousers wherein the site of a stoma is marked.
Figure 2:
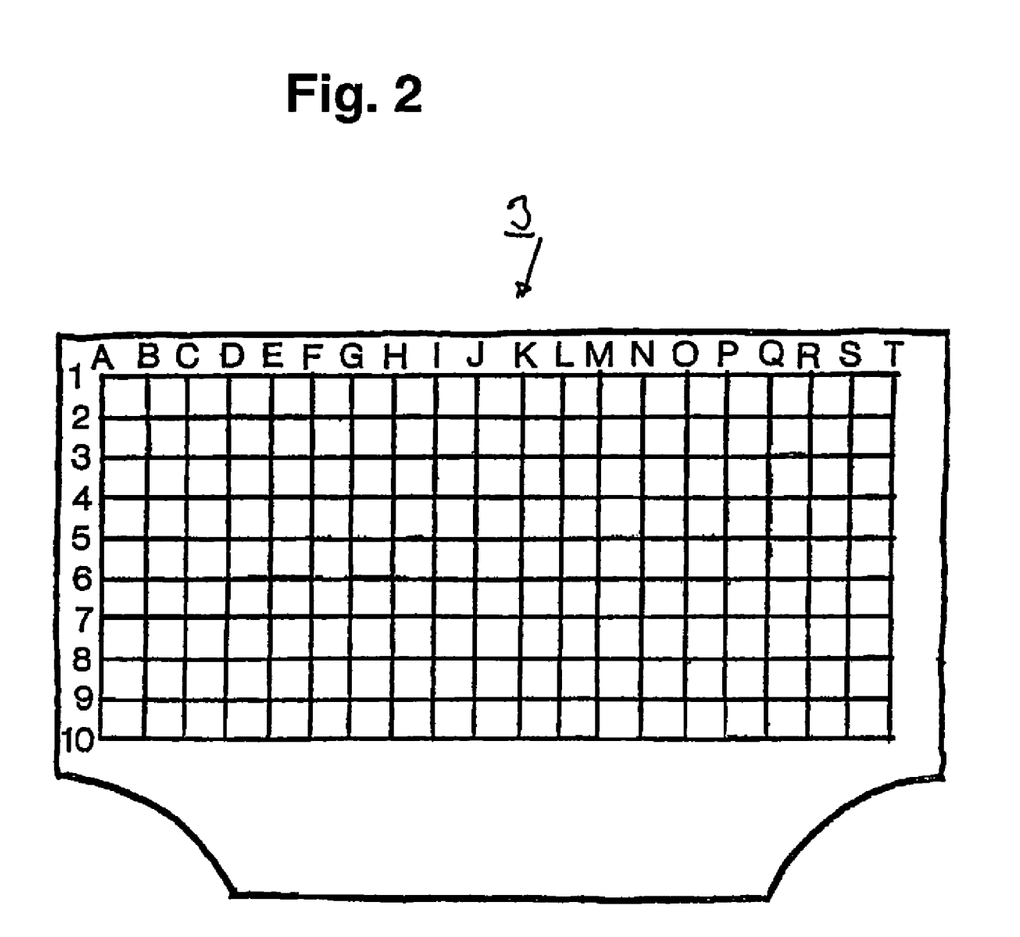
FIG. 2 shows an embodiment of the invention in the form of a stiff work piece being provided with a coordinate system.

Reference is made to FIGS. 1 and 2 which show a pair of stomal hernia trousers 1 wherein the site 2 of a stoma is marked, and an embodiment of a device 3 of the invention for locating and marking the optimum position of the centre of a hole for receiving a stoma in the form of a stiff work piece being provided with a coordinate system, having rows and columns being individually identifiable. The device in this embodiment is suitably in the form of a piece of e.g. cardboard provided with a printed coordinate system.

Figure 3:
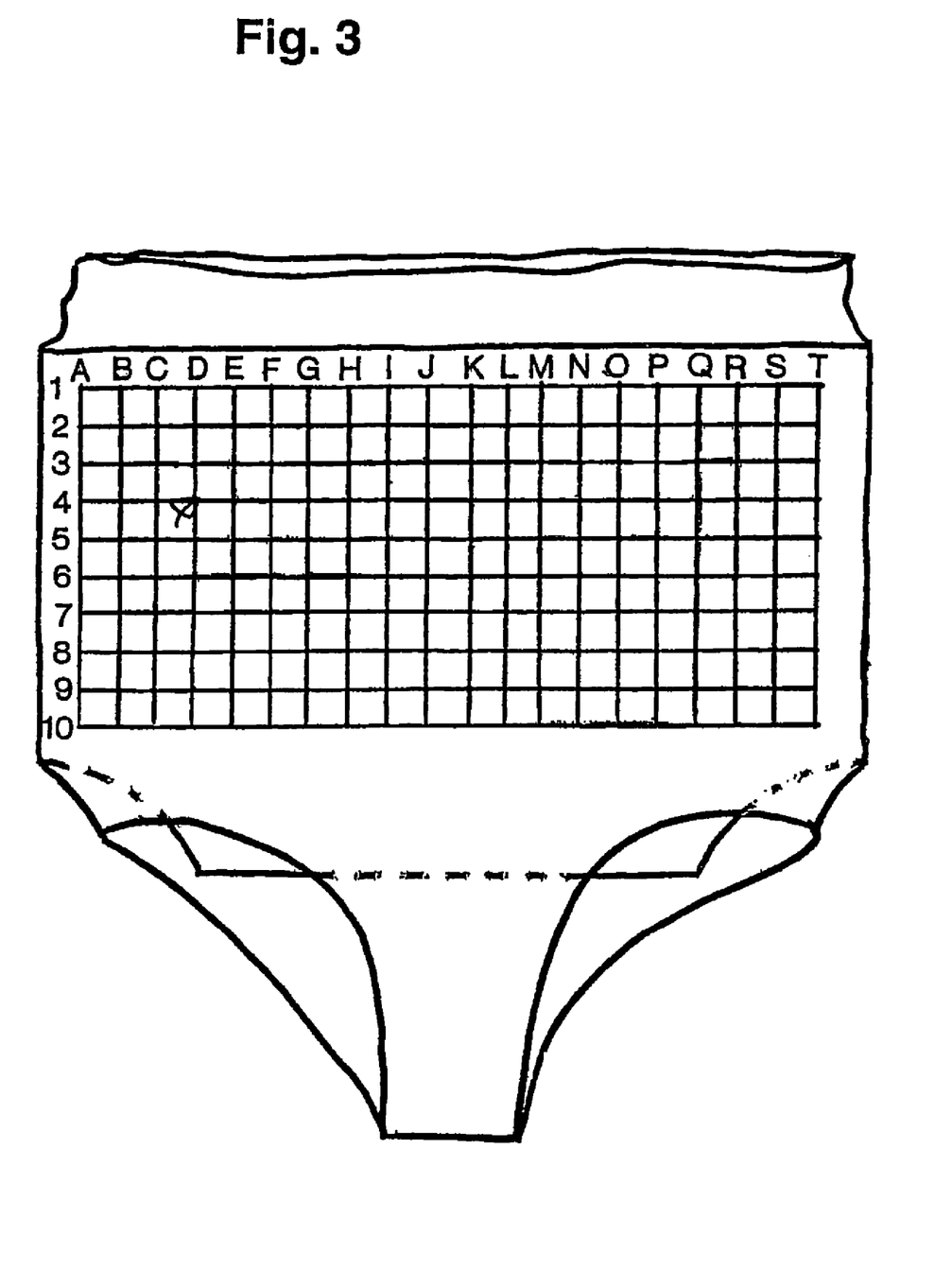
FIG. 3 shows the embodiment of FIG. 2 located in a pair of stomal hernia trousers.

FIG. 3 shows the embodiment of FIG. 2 in use located in a pair of hernia trousers on which the position of the stoma has been marked. The grid forming the coordinate system is for convenience detectable through the material of the trousers.

Figure 4:
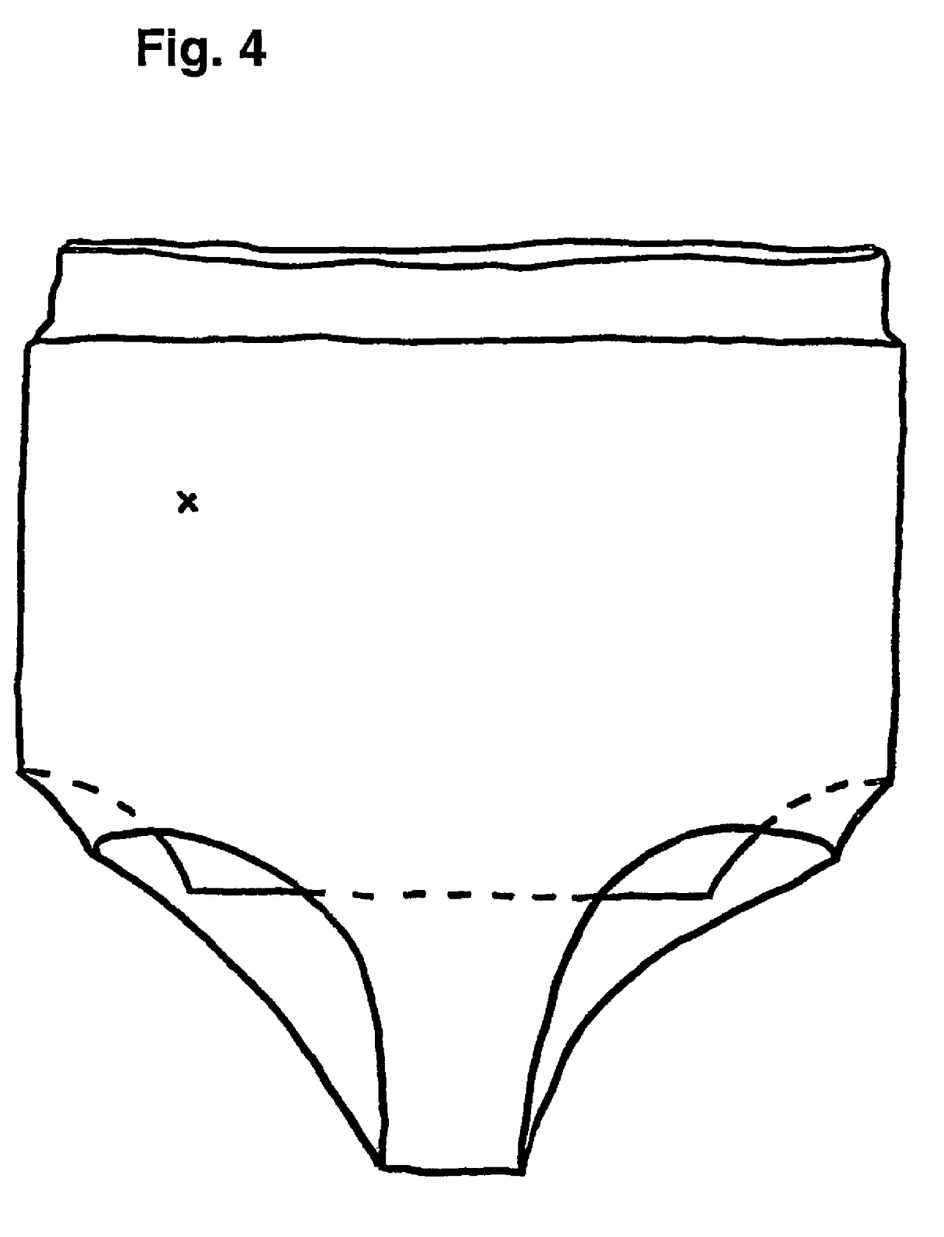
FIG. 4 shows the embodiment of FIG. 3 on which the site of the stoma has been marked.

After registration of the site and forwarding the information to the manufacturer of the stomal hernia trousers, the manufacturer places a corresponding device in a corresponding set of trousers for locating the centre of the hole to be made for tailoring the trousers to the user as indicated in FIG. 4.

Figure 5:
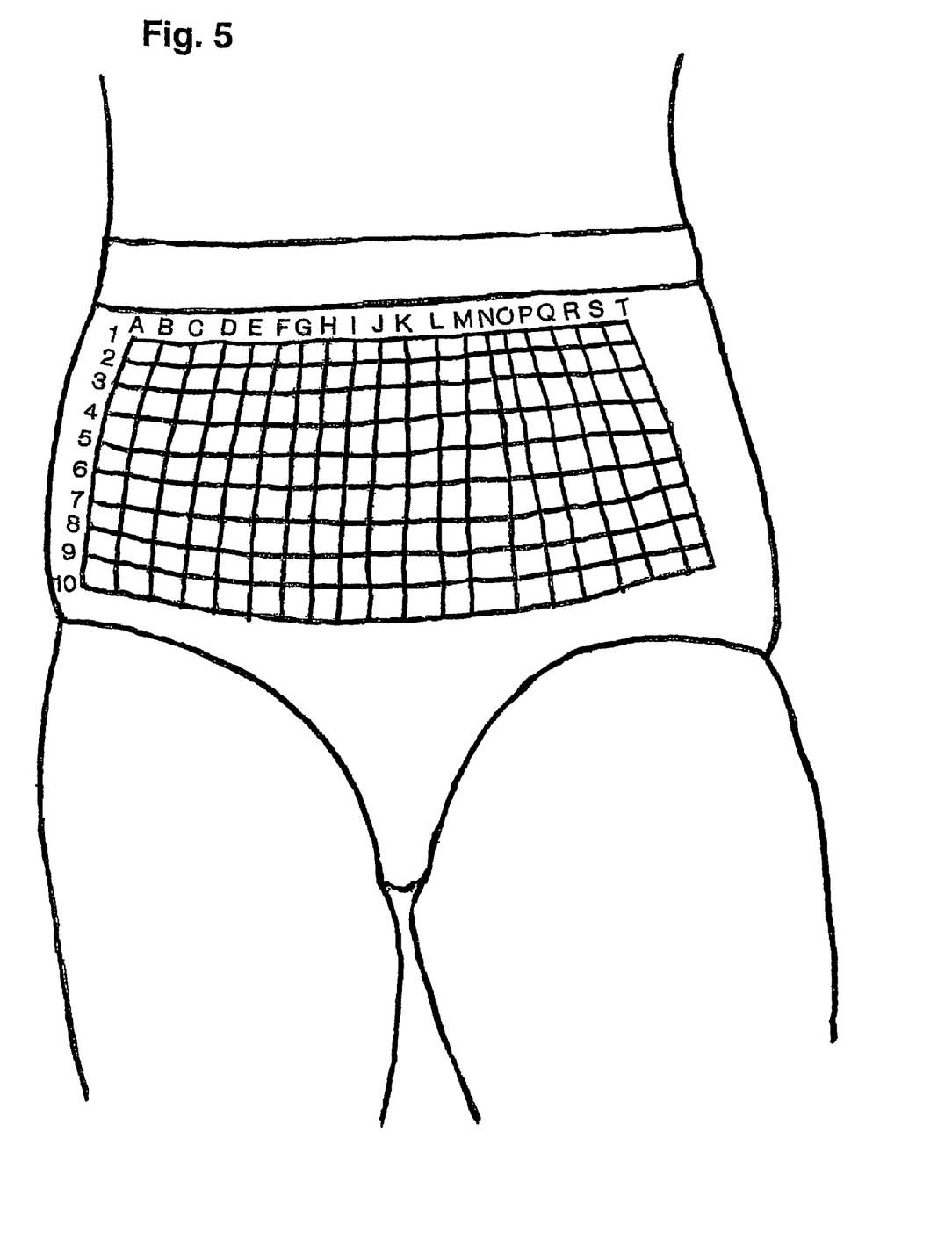
FIG. 5 shows another embodiment of the invention in the form of a pair of briefs of elastic fabric provided with a coordinate system worn by a user.

FIG. 5 shows another embodiment of the invention in the form of a pair of briefs of elastic fabric provided with a printed coordinate system and located on a user. In one embodiment, the trousers are used as test trousers for registering the site on different users whereafter the individual trousers are made in accordance with the respective registrations as indicated above.

In another embodiment, the grid or coordinate system is not only used on a set of master or test trousers but is applied on all the trousers to be used as well, printed, knitted or vowen in a discreet manner allowing an easy localisation of the centre of the hole to be made. Then, the registration may be used for a very easy marking and making the holes in the trousers to be used as the pattern is integrated in the trousers and may be used for registration from the patient and then distant therefrom directly for cutting or punching the customised hole before delivering to the user. The cutting or punching of the holes is preferably made centrally with the manufacturer or with a wholesaler in which case the manufacturing is more easily automated as the costs for the necessary equipment per produced unit is then minimized.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A combination forming a set comprising;
a pair of stomal hernia support briefs having a first portion sized and shaped to overlay an anatomical topography corresponding to multiple potential stoma locations, said briefs at least partially formed from an elastic material in the first portion so that when worn by an ostomate the elastic material is positioned and configured to provide sufficient pressure around a stoma to mechanically reposition an associated peristomal hernia; and
a work piece including a coordinate system, the work piece configured to be placed inside the hernia support briefs and having a size and shape configured to register a feature of the support briefs so as to position the coordinate system relative to and substantially encompassing the first portion.

2. The set combination according to claim 1 wherein the coordinate system is a two-dimensional coordinate system.

3. The set combination according to claim 2 wherein the coordinate system has individually identifiable rows and columns.

4. The set combination according to claim 1 wherein the coordinate system is printed on said work piece.

5. The set combination according to claim 1 wherein the coordinate system is visible through the hernia support briefs when the work piece is placed inside the hernia support briefs.

6. The set combination according to claim 1 wherein the hernia support briefs comprise a waist measurement, and a lateral width of the work piece is at least one half of the waist measurement.

7. A method for locating a centre of a hole for receiving a stoma in a manufactured stomal hernia support undergarment, the method comprising;
providing a first stomal hernia support undergarment to the ostomate;
locating and marking a position of a stoma of the ostomate on the first stomal hernia support undergarment;
removing the first stomal hernia support undergarment from the ostomate;
placing a work piece provided with a coordinate system in registration with the first stomal hernia support undergarment;
determining the coordinates in the coordinate system of the mark on the first stomal hernia support undergarment when registered to the work piece;
transferring data including a garment size and the coordinates to a manufacturer so as to manufacture a second stomal hernia support undergarment including a hole therethough positioned to receive the stoma of the ostomate wherein a location of the centre of the hole corresponds to the position indicated by the coordinates.

8. A method for locating the position of a centre of a hole for receiving a stoma of an ostomate in a manufactured stomal hernia support garment, the method comprising:
providing a first stomal hernia support undergarment having elastic fabric that includes a coordinate system to the ostomate;
determining a set of coordinates of a position of the stoma of the ostomate on the coordinate system;
transferring data including a garment size and the set of coordinates to a manufacturer so as to manufacture a second stomal hernia support garment including a hole therethough positioned to receive the stoma of the ostomate wherein a location of the center of the hole corresponds to the position indicated by the set of coordinates.

* * * * *

UNITED STATES PATENT AND TRADEMARK OFFICE
CERTIFICATE OF CORRECTION

PATENT NO. : 7,650,702 B2  Page 1 of 1
APPLICATION NO. : 10/544342
DATED : January 26, 2010
INVENTOR(S) : Henrik Jessen Jensen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1017 days.

Signed and Sealed this

Twenty-eighth Day of December, 2010

David J. Kappos
*Director of the United States Patent and Trademark Office*